United States Patent [19]

Shah et al.

[11] Patent Number: 4,892,739
[45] Date of Patent: Jan. 9, 1990

[54] OSMOTIC CONTINUOUS DISPENSING ORAL DELIVERY SYSTEM CONTAINING A PHARMACEUTICALLY ACCEPTABLE ACTIVE AGENT HAVING A IMPROVED CORE MEMBRANE ADHESION PROPERTIES

[75] Inventors: Shailesh B. Shah, Union; Arun D. Koparkar, Westfield, both of N.J.

[73] Assignee: Ciba-Geigy Corporation, Ardsley, N.Y.

[21] Appl. No.: 185,564

[22] Filed: Apr. 25, 1988

[51] Int. Cl.$^4$ .................................................. A11L 9/24
[52] U.S. Cl. ...................................... 424/473; 424/474
[58] Field of Search ............................................ 421/473

[56] References Cited

U.S. PATENT DOCUMENTS

| | | | |
|---|---|---|---|
| 3,916,899 | 11/1975 | Theeuwes et al. | 128/260 |
| 4,256,108 | 3/1981 | Theeuwest et al. | 128/260 |
| 4,326,525 | 4/1982 | Swanson et al. | 128/260 |
| 4,439,195 | 3/1984 | Swanson et al. | 604/890 |
| 4,449,983 | 5/1984 | Cortese et al. | 604/892 |
| 4,455,143 | 6/1984 | Theeuwes et al. | 604/890 |
| 4,578,075 | 3/1986 | Urquhart et al. | 604/892 |
| 4,609,374 | 9/1986 | Ayer . | |
| 4,681,583 | 7/1987 | Urqukart et al. | 424/473 |
| 4,693,886 | 9/1987 | Ayer . | |
| 4,713,248 | 12/1987 | Kjornaes et al. . | |
| 4,716,041 | 12/1987 | Kjornaes et al. . | |

FOREIGN PATENT DOCUMENTS

| | | |
|---|---|---|
| 148811 | 7/1985 | European Pat. Off. . |
| 220143 | 4/1987 | European Pat. Off. . |
| 271438 | 6/1988 | European Pat. Off. . |

OTHER PUBLICATIONS

Theeuwes et al., Br. J. Clin Pharmac. Vol. 19, pp. 69S-76S (1985).

*Primary Examiner*—Thurman K. Page
*Assistant Examiner*—Leon R. Horne
*Attorney, Agent, or Firm*—Irving M. Fishman

[57] ABSTRACT

An osmotic dispensing delivery system suitable for oral administration, containing a pharmaceutically acceptable active agent for the controlled continuous release of about 50 to about 90 percent by weight of said active agent into the gastrointestinal tract at a rate of about 5 to about 12 percent by weight of said agent per hour consisting essentially of:

(a) a shaped solid core containing an osmotically active composition comprising an effective amount of a pharmaceutically acceptable active agent, alone or in combination with a pharmaceutically acceptable binder, an osmotically active driving agent, or tabletting lubricant, or mixtures thereof;

(b) said core being substantially evenly coated with a discrete layer of a water-soluble, or water-dispersible, and water permeable substantially non-osmotically active solid polymeric binder, said binder layer being present in an amount between about 0.3 percent and about 10 percent of the weight of the core;

(c) a semi-permeable shaped wall member impermeable to said active composition and permeable to gastrointestinal fluid, surrounding and adhesively bonded to the binding layer; and (d) at least one passageway in the wall, for dispensing the active agent, in communication with said core and the external environment.

11 Claims, No Drawings

OSMOTIC CONTINUOUS DISPENSING ORAL DELIVERY SYSTEM CONTAINING A PHARMACEUTICALLY ACCEPTABLE ACTIVE AGENT HAVING A IMPROVED CORE MEMBRANE ADHESION PROPERTIES

BACKGROUND OF THE INVENTION

Osmotic delivery systems for the oral administration of drugs are well known in the art. These systems dispense the active agent in a controlled and continuous manner over a prolonged period of time to produce a desired beneficial result. Such systems are typically represented by U.S. Pat. No. 3,845,770, U.S. Pat. No. 3,916,899, U.S. Pat. No. 4,016,880 and the like.

Characteristically, such systems employ a semi-permeable shaped wall membrane capable of imbibing gastrointestinal fluid, a core compartment containing the active agent, alone or together with pharmaceutically acceptable excipients, such as binders, osmotically active driving solutes, and tabletting excipients or combinations thereof, and at least one passageway in the wall, for dispensing the active agent, in communication with the core compartment and the external environment. In the gastrointestinal tract, the device imbibes fluid through the semi-permeable membrane which fluid dissolves the active agent or the osmotically active solute, or both, to form a solution or suspension which exhibits an osmotic pressure gradient against the wall membrane. As the wall membrane is substantially impermeable to the osmotically active solution or suspension, the solution or suspension, containing the drug, passes through the passageway, or passageways in the wall to the external environment upon activation. In general, useful wall materials and device parameters for such systems are described in U.S. Pat. No. 3,916,899, the disclosure of which is incorporated by reference herein, in toto.

Unfortunately many solid pharmaceutically acceptable active agents and conventional osmotically active driving solutes possess little or no inherent binding capabilities to semipermeable membrane films. Accordingly, attempts to film coat compressed core tablets, or the like, consisting of such agents, or admixtures of such agents and driving solutes, may result in poor adhesion between the core and the semipermeable membrane. As a consequence, the semipermeable membrane coat tends to peel off the core. This problem may be aggravated when attempts are made to coat such core tablets with a semipermeable film-forming solution using conventional air suspension techniques, such as the Wurster Air suspension technique, where the core tablet may pick up a static charge, further reducing uniform adhesion between the core and resultant membrane film.

Even when relatively high amounts of conventional polymeric binders, such as poly-N-vinylpyrrolidone, poly-$C_2$-$C_3$ alkylene glycols, or hydroxy-lower alkyl-cellulose or mixtures thereof are uniformly distributed in the core composition as pharmaceutically acceptable tabletting excipients, poor adhesion between the core and membrane coating, resulting in delamination or membrane peeling, may be characteristically observed.

Also, the use of excessive amounts of conventional polymeric binders is generally undesirable where the unit dosage amount desired for the particular pharmaceutically acceptable active agent employed is sufficiently great that the cores employing such large amounts of binder exceeds the size for convenient oral unit dose administration to the warm blooded mammalian host. Moreover, excessive amounts of conventional polymeric binders can interfere with the desired continuous release profile of the active agent in the core by excessively retarding the dissolution and release of the active agent in the gastrointestinal tract or by clogging the one or more passageways, thereby occasioning potential rupturing of the device.

Surprisingly and unexpectedly, it has now been discovered that the active agent containing core may be substantially evenly coated with a thin discrete layer of a water-soluble, or water-dispersible, and water permeable substantially non-osmotically active solid polymeric binder, which treated core can thereafter be coated with semi-permeable membrane material which adhesively binds to the binding layer, to form a stable laminated osmotically activated device substantially free from the aforementioned defects.

OBJECTS OF THE INVENTION

It is accordingly an object of the invention to provide an osmotic delivery system for the oral administration of a pharmaceutically acceptable active agent to a warm blooded animal, comprising a shaped solid core comprising said active agent, coated with a discrete layer of water-soluble, or water dispersible, and water permeable substantially non-osmotically active solid polymeric binder, a semi-permeable shaped wall surrounding and adhesively bonded to said layer of binder, and at least one passageway in said wall in communication with the core and the external environment of use, for dispensing the active agent in a controlled continuous manner into the gastrointestinal tract.

It is a further object of the present invention to provide a method for continuously administering an active agent to a warm blooded mammal at a controlled rate comprising admitting to the gastrointestinal tract such a device.

These and other objects of the instant invention are more fully described in the following detailed disclosures.

DETAILED DESCRIPTION OF THE INVENTION

One embodiment of the present invention relates to an osmotic dispensing oral delivery system, suitable for administration to a warm blooded mammalian host, containing a pharmaceutically acceptable active agent for the controlled continuous release of about 50 to about 90 percent by weight of said active agent into the gastrointestinal tract at a rate of about 5 to about 12 percent by weight of said agent per hour consisting essentially of:

a) a shaped solid core containing an osmotically active composition comprising an effective amount of a pharmaceutically acceptable active agent, alone or in combination with a pharmaceutically acceptable binder, an osmotically active driving agent, or a tabletting lubricant, or mixtures thereof;

b) said core being substantially evenly coated with a discrete layer of a water-soluble, or water-dispersible, and water permeable substantially non-osmotically active solid polymeric binder, said binder layer being present in an amount between about 0.3 percent and about 10 percent of the weight of the core;

c) a semi-permeable shaped wall member impermeable to said active composition and permeable to gastrointestinal fluid, surrounding and adhesively bonded to the binding layer; and d) at least one passageway in the wall, for dispensing the active agent in the gastrointestinal tract, in communication with said core and the external environment.

The shaped solid core contains 5-20 wt %, preferably 8 to 10 wt % of a binder, 0-5 wt % preferably 1-5 wt %, more preferably 2-4 wt % of a tabletting lubricant, 0-80 wt % preferably 0-45 wt %, more preferably 0-20 wt % of an osmotically active driving agent and the remainder of a moderately water soluble pharmaceutically acceptable active agent, all based on the total core composition weight.

The moderately water soluble active agent is advantageously a β-blocker, preferably metoprolol, more preferably a pharmaceutically acceptable salt of metoprolol, most preferably metoprolol fumarate. The moderately water-soluble active agent is one such that it dissolves in the aqueous environment upon activation in the environment of use, i.e. the gastrointestinal tract, by aqueous fluid being imbibed by diffusion through the semipermeable shaped wall and permeable binder into the core compartment to continuously form a concentrated osmotically active solution of pharmaceutically active agent. The concentrated salt, or solute, solution exhibits an osmotic pressure gradient against the aqueous gastrointestinal fluid and is released through one or more passageways in the wall in communication with both the core compartment and the external environment, to dispense the pharmaceutically active agent at a controlled, preferably generally constant rate. The influx of aqueous fluid from the environment through the semipermeable wall is generated by an osmotic pressure gradient and causes the continuous dissolution of the pharmaceutically active agent containing composition in the core of the device. Accordingly, the pharmaceutically active agent chosen is advantageously one which possesses only limited or moderate solubility in the imbibed aqueous fluid, such that the active agent is released in a continuous manner over a prolonged period of time by maintaining the rate of internal dissolution of the core composition.

Preferably, the pharmaceutically active agent exhibits a solubility in water of 0.1 to about 0.6 g/cc at about 37° C. which can be determined simply by dissolving the pharmaceutically active agent in water. Typically pharmaceutically acceptable salts of the pharmaceutically active agent are employed, and include without limitation, for example, basic materials: lower alkanoates of mono and di carboxylic acids such as fumarate, maleate, and acetate, most preferably fumarate.

Suitable tabletting lubricants include, for example, those known in the art such as silicas, corn starch, talc, magnesium stearate, stearic acid, and high molecular weight polyethylene glycols, preferably magnesium stearate.

The osmotically active driving agent, when present, is typically a sugar alcohol such as mannitol or sorbitol, or sugars in combination with polysaccharides such as destrose and maltose a physiologically tolerable ionic salt which is compatible with the other components such as sodium or potassium chloride, or urea. Many others known to those of ordinary skill may be chosen and will be suitable.

The binder component is usually selected from any of the typical tabletting binders used in the tabletting art; however, it is advantageously a poly-N-vinylpyrrolidone, most preferably having a molecular weight of 10,000 to 60,000. Povidone USP is preferred, which is commercially available under the tradename "Plasdone" from GAF. The binder, while it need not be present in the core at all, is preferably used in amounts of 5-20% most preferably 8.5-15%, still more preferably 8-10% most preferably 8.5-13% by weight based upon the total core weight.

The cores described above have a thin film binder layer coated thereon which ranges from 0.3 to 10% preferably 0.5-2% by weight based on the core. Essentially any known film forming binder which is pharmaceutically acceptable will be suitable. Still, preferred materials include, but are not limited to hydroxypropylmethylcellulose, polyvinylpyrrolidone, hydroxypropylcellulose, hydroxyethyl cellulose, methylcellulose, polyethyleneglycol, poloxamers, and reverse poloxamers. The polyethyleneglycols are suitably of 400-8,000 weight average molecular weight, while the cellulose derivatives are of a viscosity grade of from 3 to 4000 cps. Mixtures of the above film forming binders are also suitable, preferably at least 50% hydroxypropylmethylcellulose, and most preferably hydroxypropylmethylcellulose in combination with lesser amounts of polyethylene glycol and/or polyvinylpyrrolidone. In addition, the film forming binder layer can also contain up to 10% of an anti-tacking agent, most notably talc or titanium oxide, most preferably up to 10% by weight based on the total film forming binder layer; however, it is preferably absent. The anti-tacking agents, when used typically have an average particle size of less than 25 microns.

The semipermeable wall membrane is a material which can form films and does not adversely affect the active agent, preferably metoprolol salt, or host, and is permeable to the external gastrointestinal fluid while essentially impermeable to the active agent, preferably metoprolol salt, in the device. The selectively permeable membrane forming the wall is insoluble in the gastrointestinal tract and non-erodible or it can be bioerodible after a predetermined period with bioerosion corresponding to the end of the active drug release period. In each instance it is semipermeable to the gastrointestinal solvent but not to the active agent solute and is suitable for construction of the osmotic powered device. Typical materials for forming the wall include membranes known to the art as osmosis and reverse osmosis membranes, such as commercially available unplasticized cellulose acetate, plasticized cellulose triacetate, agar acetate, amylose triacetate, beta glucan acetate, beta glucan triacetate, cellulose acetate ethyl carbamate, cellulose acetate phthalate, cellulose acetate methyl carbamate, cellulose acetate succinate, cellulose acetate dimethylaminoacetate, cellulose acetate ethyl carbonate, cellulose acetate methyl sulfonate, cellulose acetate butyl sulfonate, cellulose ethers, cellulose acetate propionate, poly(vinyl methyl) ether polymers, cellulose acetate octate, cellulose acetate laurate, methyl cellulose, cellulose acetate p-toluene sulfonate, ethyl cellulose, triacetate of locust bean gum, cellulose acetate with acetylated hydroxyethyl cellulose, hydroxylated ethylenevinylacetate, osmotic membranes made from polymeric epoxides, alkylene oxide-alkyl glycidyl ethers, polyurethanes, polyglolic acid, and polycationpolyanion membranes known in the art. Generally, such membranes having a fluid permeability of between about 0.01 to 10 cc/cm$_2$×hour or day or higher at atmospheric pressure against a saturated product solution at about 30° C., and simultaneously possessing a high degree of impermeability to the metoprolol salt solution are useful.

Preferred semipermeable membrane materials include polyurethanes, methyl cellulose, cellulose acetate, ethyl cellulose, and cellulose acetate butyrate. Most preferred is cellulose acetate.

In general, useful wall materials and device parameters are disclosed, for example, in U.S. Pat. No. 3,916,899, the disclosure of which is incorporated by reference herein, in toto.

In a preferred embodiment, the pharmaceutically active agent is a metoprolol salt. The amount of metoprolol salt, expressed as metoprolol, present in the core, can vary widely but is preferably between about 25 to about 500 mg per unit tablet device. Preferably, the core contains between about 30 to about 400 mg of metoprolol, more preferably 40 to 400 mg of metoprolol, still more preferably 200-400 mg metoprolol, yet even more preferably 200-400 mg metoprolol, most preferably 250-400 mg metoprolol, each in the form of a salt.

The metoprolol salt containing device is suitable for treating those conditions in mammals, including man, responsive to beta$_1$-adrenoreceptor blocking agents. Preferred indications include the treatment of those indications for which metoprolol and its pharmaceutically acceptable salts are known to be useful, including hypertension, angina pectoris, cardiac arrhythmias, and in the treatment of hemodynamically stable patients with myocardial infarction to reduce cardiovascular mortality. Devices of the invention containing other active agents are suitable for treating those conditions for which such active agent is known to be useful.

Conventional commercially available metoprolol tartrate has an immediate release profile and is not in a rate controlled continuous dispensing form. On multiple dosing, such non-continuous forms produces fluctuations between peaks and troughs in terms of blood-plasma levels as well as the degree of beta-blockade. While more frequent administration of such conventional forms can reduce these fluctuations, it is burdensome to some patients and may lessen compliance. While single, daily doses of the conventional metoprolol salt are adequate if the only aim is to reduce blood pressure, a three-times-a-day regimen is advisable to control arrhythmias, and a twice-a-day regimen is advisable for the maintenance phase for the respective indications of myocardial infarction and angina pectoris.

The instant device advantageously provides a once-a-day regimen for all of the above indications for the total release, per unit dose, of between about 25 and about 500 mg of active agent, preferably metoprolol, more preferably from about 30 to about 500 mg of metaprolol base in the form of a salt, most preferably in the form of the fumarate salt, wherein from about 50 up to about 90 percent of said active agent is released at a substantially continuous rate of about 5 to about 12 percent by weight per hour.

The core compartment is in the form of a tablet which is film coated with a film forming binder and this "coated core" is film coated with the semipermeable membrane to form the wall. The core composition is advantageously prepared by combining the moderately water-soluble pharmaceutically active agent, preferably a salt of metoprolol, with the tabletting binder, preferably poly-N-vinylpyrrolidone, either by dry blending and granulating in the presence of a water or ethanol or water-ethanol mixture or by mixing said pharmaceutically active agent with an aqueous, ethanolic, or aqueous-ethanolic solution of tableting binder (i.e. poly-N-vinylpyrrolidone or hydroxy propylmethylcellulose or a mixture thereof), subsequently granulating the mixture, then drying the granulation and milling the same and optionally blending the dried milled granules with a tableting lubricant, and finally compressing the resulting granules into tablets to form the core.

The core is then thinly coated with a solution of hydroxypropylmethylcellulose or other film forming binder material and the coated core tablet is then subsequently coated with a semi-permeable film-forming solution using conventional film coating techniques, such as the Wurster Air suspension technique or coating pan, to obtain the core tablet within the semipermeable shaped wall. The resulting device is provided with at least one passageway to osmotically release the metoprolol salt, as a concentrated or saturated solution, from the core to the gastrointestinal tract at a controlled rate. The passageway(s) can be formed, in situ, by using a heterogeneous solution to coat the core tablet containing the semipermeable membrane film-forming solution and a water or gastrointestinal fluid soluble material, whereby in the environment of use passageways are formed in situ, or the semipermeable shaped wall can be drilled, either mechanically or by use of a laser, to form the passageway or passageways.

The passageway orifice size will vary depending upon the size of the core, exact desired release profile, and the number of passageways. Where one passageway is present, the orifice size can vary, for example, between about 0.1 mm and about 0.8 mm.

Generally, the film forming semipermeable wall material is applied to the coated tablet core in the form of an organic solvent containing solution. Suitable solvents include, for example, dioxane, diethyl ether, lower alkanols, such as methanol or ethanol, and halogenated lower alkanes, such as chloroform, methylchloride and methylene chloride, or mixtures thereof. The amount of semipermeable membrane material employed per unit dose will vary dependent upon, for example, the permeability characteristics of the membrane material. For example, using cellulose acetate as the film-forming material, between about 4 and about 30 percent by weight, preferably between about 10 to about 20 percent by weight based upon the total weight of the device, may be employed.

The following examples are merely illustrative of the present invention and should not be considered as limiting the scope of the present invention. All parts are by weight unless otherwise specified.

EXAMPLE 1

3800 g of metoprolol fumarate and 190 g of hydroxypropylmethyl cellulose are separately screened to 30 mesh and 16 mesh, respectively. The screened materials are then blended together, and the blend is granulated with 1000 ml of a 10% w/v solution of polyvinylpyrrolidone in a 70:30 volume mixture of ethyl alcohol and water. The granules are then dried for 16 hours in an oven at 40° C. and the dried granules are milled and blended with 120 g of magnesium stearate and finally compressed into cores.

56.0 g of hydroxypropylmethyl cellulose are dissolved in 750 ml of methylene chloride/methanol and the solution is used to uniformly coat the cores using fluidized bed apparatus, 24 g of hydroxypropylmethyl cellulose, 24 g of polyethylene glycol and 252 g of cellulose acetate are dissolved in 5000 ml of methylene chloride/methanol and the solution is used to further uniformly coat the hydroxypropylmethyl cellulose coated cores in a fluidized bed apparatus. The coated tablets are then drilled to result in a bore of about 0.34 mm diameter connecting the uncoated core with the outside environment.

EXAMPLES 2-10

The procedure of Example 1 is followed except that the variations in the Table below are introduced.

| active agent | g | core binder (g) | core granulator (g) | subcoat (g) |
|---|---|---|---|---|
| 2. metoprolol fumarate | (3800) | | | |
| 3. metoprolol tartrate | (4000) | | | |
| 4. | | HPC (190) | | |
| 5. | | | HPMC (190) | |
| 6. | | HPMC (380) | | |
| 7. | | | HPC (190) | |
| 8. | | HEC (190) | | |
| 9. | | PVP (400) | | HPMC (30) |
| 10. | | | | HPMC (28)/ PVP (28) |

What is claimed is:

1. An osmotic dispensing oral delivery system containing a moderately water-soluble pharmaceutically active agent a B-blocker wherein upon activation in the gastrointestinal tract of the host, from about 60 up to about 90 percent of said active agent is delivered at a substantially continuous rate of about 5 to about 12 percent by weight of the total weight of said active agent, per hour, comprising:
   (a) a semipermeable shaped wall membrane substantially impermeable to said pharmaceutically active agent and permeable to gastrointestinal fluid;
   (b) a discrete layer within said wall membrane of a water-soluble or water dispersible but water permeable substantially non-osmotically active solid polymeric binder in an amount of from 0.3 to 10% by weight based on a core;
   (c) said core within and defined by said discrete binder layer, said core being in the form of a solid osmotically active composition comprising about 5 to about 20 percent by weight of a tableting binder; 0 up to about 10 percent by weight of a tableting lubricant; 0 up to 80% by weight of an osmotically active driving agent; and the remainder said pharmaceutically active agent all based upon the total core composition weight; and
   (d) at least one passageway in said wall in communication with said core and the external environment for dispensing said active agent into said gastrointestinal tract.

2. The system of claim 1 wherein the β-blocker is metoprolol or a salt thereof.

3. The system of claim 2, wherein the β-blocker is a metoprolol salt.

4. The system of claim 3 wherein the metoprolol salt is metoprolol fumarate.

5. A system according to claim 1, wherein the wall membrane consists essentially of cellulose acetate.

6. A system according to claim 1, wherein the core contains between about 25 and about 500 mg of metoprolol base as a salt.

7. The system of claim 6 wherein the core contains 30 to 400 mg of metoprolol base as a salt.

8. A system according to claim 1, wherein the core contains between about 1 and about 5 weight percent of tableting lubricant.

9. A system according to claim 8, wherein the tabletting lubricant is magnesium stearate.

10. The system of claim 1 wherein the tabletting binder is hydroxypropyl methylcellulose or polyvinylpyrrolidone or mixtures thereof.

11. The system of claim 1 wherein the polymeric binder in the discrete layer of polymeric binder is hydroxypropylmethylcellulose, polyvinylpyrrolidone or mixtures thereof and 0% up to a total of 50% of polyethyleneglycol.

* * * * *